(12) United States Patent
Suzuki et al.

(10) Patent No.: US 6,849,576 B2
(45) Date of Patent: Feb. 1, 2005

(54) PLANT-ACTIVATING AGENT

(75) Inventors: Tadayuki Suzuki, Wakayama (JP); Toshio Hayashi, Wakayama (JP); Masaharu Hayashi, Osaka (JP); Masatoshi Kamei, Wakayama (JP); Kazuhiko Kurita, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/842,770

(22) Filed: Apr. 27, 2001

(65) Prior Publication Data

US 2002/0006872 A1 Jan. 17, 2002

(30) Foreign Application Priority Data

Apr. 28, 2000 (JP) ...................................... 2000-131670

(51) Int. Cl.[7] .............................................. A01N 61/00
(52) U.S. Cl. .................... 504/116.1; 504/117; 504/118; 504/320; 504/335; 504/353
(58) Field of Search .............................. 504/116.1, 117, 504/118, 320, 335, 353; 71/1

(56) References Cited

U.S. PATENT DOCUMENTS

| | | | |
|---|---|---|---|
| 4,436,547 A | * 3/1984 | Sampson | 71/76 |
| 4,481,202 A | 11/1984 | Johnston | 424/250 |
| 4,681,900 A | 7/1987 | Iwasaki | 514/786 |
| 5,510,322 A | 4/1996 | Young | |
| 5,549,729 A | * 8/1996 | Yamashita | 71/26 |
| 5,693,592 A | 12/1997 | Illingworth | 504/118 |
| 6,004,906 A | * 12/1999 | Sakagami et al. | 504/350 |
| 6,121,195 A | 9/2000 | Nonomura et al. | 504/136 |

FOREIGN PATENT DOCUMENTS

| | | |
|---|---|---|
| CN | 1177582 | 4/1998 |
| DE | 3234610 A1 | 3/1984 |
| DE | 3724595 A1 | 2/1989 |
| DE | 4445546 A1 | 6/1996 |
| EP | 0025141 A1 | 3/1981 |
| EP | 0161114 A2 | 11/1985 |
| EP | 0167026 A1 | 1/1986 |
| EP | 0718405 A2 | 6/1996 |
| EP | 0823994 A1 | 2/1998 |
| EP | 0998850 A1 | 5/2000 |
| EP | 1046625 A2 | 10/2000 |
| FR | 2780972 A1 | 1/2000 |
| JP | 61183202 A | 8/1986 |
| JP | 08157317 A | 6/1996 |
| JP | 2000159591 A | 6/2000 |
| JP | 2001026505 A | 1/2001 |
| JP | 2001-058910 A | 3/2001 |
| RU | 2101953 C | 1/1998 |
| WO | WO 83/03041 | 9/1983 |
| WO | WO87/03780 | 7/1987 |
| WO | WO94/00009 | 1/1994 |
| WO | WO96/14749 | 5/1996 |
| WO | 0718405 A3 | 6/1996 |
| WO | WO 96/19111 | 6/1996 |
| WO | WO96/25851 | 8/1996 |
| WO | WO96/28026 | 9/1996 |
| WO | WO96/41530 | 12/1996 |
| WO | WO96/41531 | 12/1996 |
| WO | WO96/41532 | 12/1996 |
| WO | WO97/00614 | 1/1997 |
| WO | WO97/08951 | 3/1997 |
| WO | WO99/01032 | 1/1999 |
| WO | WO99/11132 | 3/1999 |
| WO | WO99/12417 | 3/1999 |
| WO | WO99/63819 | 12/1999 |
| WO | WO 00/02451 | 1/2000 |
| WO | WO00/02454 | 1/2000 |
| WO | WO00/25582 | 5/2000 |
| WO | WO00/47046 | 8/2000 |
| WO | WO 0063138 | 10/2000 |
| WO | WO01/82698 A1 | 11/2000 |
| WO | WO 01/58262 A1 | 8/2001 |
| WO | WO 01/64832 A2 | 9/2001 |
| WO | WO02/055480 A2 | 7/2002 |

OTHER PUBLICATIONS

Fundamentals of Machine Operation. John Deere Co. Chapter 2, "Fertilizers and Lime". p. 16–35. 1976.*

Reddy et al., Biochimica et Biophysica Acta; vol. 1483, pp. 294–300, (2000).

Ozeretskovskaya et al., Fiziologiya Rastenii, vol. 41, No. 4, pp. 626–633, (1994), abstract.

Watanabe et al., Plant and Cell Physiology, vol. 37, No. 2, pp. 147–151, (1996), abstract.

Conconi et al., Nature, vol. 383, No. 6603, pp. 826–829, (1996), abstract.

Chaney et al., Proc. West. Plant Growth Regul. Soc. vol. 12, pp. 18–25, (2000), abstract.

Ulbright et al., Dissertation Abstracts International, vol. 41, No. 3, pp. 761, (1980), abstract.

Byers et al., Hortscience, vol. 11, No. 5 pp. 506–507, (1976), abstract.

Berrie et al., Plant Science Letters, vol. 6, No. 3, pp. 163–173, (1976), abstract.

Ryan et al., Combined Preceedings of the Intl. Plant Prop. Soc., vol. 23, pp. 88–95, (1973), abstract.

Isogai et al., Agric. Biol. Chem., vol. 48, No. 10, pp. 2607–2609, (1984), abstract.

Goto et al., J. of Jap. Soc. For Hort. Science, vol. 68, No. 4, pp. 762–767, (1999), abst.

(List continued on next page.)

*Primary Examiner*—S. Mark Clardy
(74) *Attorney, Agent, or Firm*—Birch, Stewart, Kolasch & Birch, LLP

(57) ABSTRACT

The present invention provides a plant-activating agent which does not cause chemical injury on plants and which improves efficiently the activity of plants. The present invention uses a substance having not less than 5% of an improved degree in reproduction of green cells measured by a specific method as the plant-activating agent.

24 Claims, No Drawings

OTHER PUBLICATIONS

Greany et al., Florida Entomologist, vol. 76, No. 2, pp. 258–263, (1993), abst.
Tsoneva et al., Fiziologiya na Rasteniyata, vol. 17, No. 2, pp. 9–17, (1991), abst.
Philosoph–Hadas et al., Advances in Agricultural Bio., No. 26, pp. 135–142, (1989), abst.
Peng et al., ACTA Phyto. Sinica, vol. 13, No. 2, pp. 182–189, (1987), abst.
Shindo et al., Meiji Daigaku Nog. Ken. Hokoku, vol. 66, pp. 1–17, (1984), abst.
Bezdek, V., Rostlinna Vyroba, vol. 18, No. 1, pp. 43–51, (1972), abstract.
Molyavko et al., Karant Rast., No. 9, p. 21, (1998), abst.
Arnone et al., Phytochemistry, vol. 28, No. 10, p. 2803–2806, (1989), abst.
Min et al., J. of Plant Growth Regulation, vol. 15, No. 3, pp. 121–128, (1996), abst.
Kato et al., Bioscience, Biotechnology and Biochem., vol. 60, No. 1, pp. 34–38, (1996), abst.
Amano et al., Fisheries Science, vol. 60, No. 4, pp. 449–454, (1994), abstract.
Belles et al., Molecular Plant–Microbe Inter., Vo. 12, No. 3, pp. 227–235, (1999), abst.
Sanaullah et al., Bangladesh J. of Botany, vol. 28, No. 2, pp. 139–144, (1999), abst.
Lone et al., Tests of Agro. and Cult., No. 20, pp. 36–37, (1999), abst.
Filippova et al., Rol. Mikroelem. Prot. Rosta Razvit. Rast, vol. 1963, pp. 119–122, (1965), abst.
Oostendorp et al., Euro. J. of Plant Pathology, vol. 107, No. 1, pp. 19–28, (2001), abst.
Tosi et al., Euro. J. of Plant Pathology, vol. 106, No. 8, pp. 735–744, (2000), abst.
Tanaka et al., Nippon Noyaku Gakkaishi, vol. 25, No. 2, pp. 133–139, (2000), abst.
Sasaki, K., Biohydrogen, pp. 133–142, (1998), abst.
Mickevicius et al., Biologija, vol. 1, pp. 29–34, (1999), abst.
Jokinen et al., Acta Horticulturae, vol. 487, pp. 233–236, (1998), abst.
Kinnersley et al., Proceedings of the Plant Growth Reg. Soc., 25$^{th}$ Edition, pp. 89–94, (1998), abst.
Cronan et al., Natural Product Letters, vol. 11, No. 4, pp. 271–278, (1998), abst.
Makela et al., Ind. Crops and Products, vol. 7, No. 2,3, pp. 139–148, (1998), abst.
Nagaoka, M. et al.; "Effect of Efficacy Accelerator based on Complex of Surfactants with Liquid Fertilizer on the Early Growth of Vegetables"; Journal of Horticulture Association, vol. 68, Suppl. 2, Oct. 1999; pp. 1–18.

* cited by examiner

PLANT-ACTIVATING AGENT

TECHNICAL FIELD OF THE INVENTION

The present invention relates to a plant-activating agent which is given and used in the state of solution, paste or solid to roots, stems, phylloplanes or fruits of a plant by methods such as spraying onto phylloplanes, spraying onto soil, water-introduction into soil, irrigating into soil and the like, or a method of adding to a culturing solution of hydroponics etc. Now, hereinafter, the term of "plant" means products that can be recognized from the term itself, vegetables, fruits, fruit trees, crops, seeds, bulbs, flowers, grass, herbs, plants defined in taxonomy, and so on.

PRIOR ART

Various nutrient elements are necessary for growth of plants. It is known that lack of some of the elements causes the hindrance of the growth of the plants. For example, the big three fertilizer components function as follows. Nitrogen is a component element of proteins, and phosphorus not only is a formation element of nucleic acid or phospholipid but also plays an important part in energy metabolism and synthetic or decomposing reaction of a substance. Potassium has a physiological action of substance metabolism or substance migration. If these main components lack, the growth of plants generally becomes poor. Calcium is an important component constituting plants and cells, and further plays an important part in maintenance of the balance of the metabolic system. The lacking state of calcium causes physiological troubles. Besides, various nutrients as follows are necessary for plants: Mg, Fe, S, B, Mn, Cu, Zn, Mo, Cl, Si, Na and the like.

Nutritious components such as nitrogen, phosphorus and potassium are applied as basal fertilizer or additional fertilizer. Alternatively, they are applied by diluting liquid fertilizer and irrigating the diluted fertilizer into soil or by spraying the diluted fertilizer onto phylloplanes. These fertilizers are necessary and/or essential for the growth of plants. However, even if they are applied at larger concentrations than some values, the growth of plants and the yield of the plants cannot be further improved.

However, it is an important theme in agricultural production to promote the growth of agricultural plants and to increase the yield per unit area to strive for an increase in income. Various plant growth regulators being necessary for this theme have been developed and used. The plant growth regulators, the typical examples of which include gibberellin, cytokinin, abscisic acid, brassinolide, auxin and ethylene are used to regulate growth reaction or form-producing reaction such as germination, rooting, expansion, flowering and bearing. The actions of these substances are many-sided and complicated. The uses thereof are restrictive.

As a result of application in a large amount of fertilizer into the soil for an increased yield of the products, various components may become excessive in the soil so that the balance of absorption thereof may become bad or the growth of plants may be delayed. Then, there arise, for example, problems that the increased yield as an aim cannot be attained or the quality such as sugar concentration (Brix. value) does not rise. Further, since there is a limit of nutrient absorption from roots, direct absorption of necessary fertilizer elements from phylloplanes or fruits may be attempted by spraying an aqueous solution or aqueous suspension of the elements. However, even if the aqueous solution of the necessary elements is merely sprayed onto phylloplanes, a problem arises from the viewpoint of absorption efficiency. Spraying excessive amounts of fertilizer elements imposes stress on plants resulting chemical injury.

Because of such conditions, there is desired a plant-activating agent which does not cause e.g. chemical injury on plants, of which use is not restricted, and which shows an excellent effect of reinforcing growth on plants.

DISCLOSURE OF THE INVENTION

The present invention relates to a plant-activating agent comprising a substance having not less than 5% of the improved degree in reproduction of green cells calculated by the following formula:

$$\text{Improved degree in reproduction of green cells } (\%) = [(P_1 - P_0)/P_0] \times 100$$

$P_0$: Reproduction amount of green cells when a substance acting as the plant-activating agent is not used, and $P_1$: Reproduction amount of green cells when a substance acting as the plant-activating agent is used.

Further, the present invention relates to a plant-activating agent comprising a substance having not less than 5% of the improved degree in reproduction of green cells calculated by the following formula and satisfying at least one of the following (a), (b), (c), (d) and (e):

$$\text{Improved degree in reproduction of green cells } (\%) = [(P_1 - P_0)/P_0] \times 100$$

$P_0$: Reproduction amount of green cells when a substance acting as the plant-activating agent is not used, and $P_1$: Reproduction amount of green cells when a substance acting as the plant-activating agent is used; and (a) Improved degree of the chlorophyll value (hereinafter, abbreviated as SPAD value) is not less than 2 points, (b) Increased amount in weight of a plant (fresh weight or dry weight) is not less than 10%, (c) Improved degree in leaf-area of a plant is not less than 5%, (d) Increased amount in concentration of ascorbic acid in the blade part is not less than 5%, and (e) Decrease degree in concentration of nitrate ion in the blade part is not less than 10%.

It is preferable that the above-mentioned substance has not less than 5% of a standard improved degree in reproduction of chlorella (whose measuring method is described in this description).

The above-mentioned substance is specifically at least one selected from the group consisting of (1) fatty acids or derivatives thereof, (2) organic acids or derivatives thereof, (3) lipids or derivatives thereof, (4) alcohols or derivatives thereof, (5) amines or derivatives thereof, (6) amino acids or derivatives thereof, (7) proteins or derivatives thereof, (8) nucleic acids or derivatives thereof, (9) terpenes or derivatives thereof, (A) natural extracts, (B) fermentation products, (C) fermentation residues and (I) vitamins.

Further, there is provided a plant-activating composition comprising the above-described substance and at least one selected from surfactants and chelating agents.

Also, the present invention relates to use of the above-described substance as a plant-activating agent and relates to a method of activating a plant, which comprises applying the above-described substance to the plant.

MODES FOR CARRYING OUT THE INVENTION

In the present invention, the improved degree in reproduction is measured by the reproduction amount of cells when green cells are cultivated under the same condition, namely, by the number and weight of cells. Now, "green cell" is a cell which has chloroplast and which can photosynthesize, and may be derived from any of unicellular organisms and multicellular organisms, however, does not include an individual itself of a multicellular organism. In case of a unicellular organism, an individual of this organism can be used itself as a green cell. In the present invention, a unicellular green cell (e.g. algae) is preferably used and chlorella (*Chlorella vulgaris*) is preferably used in particular. When chlorella is used, a test substance acting as a plant-activating agent is added to an inorganic salt medium for chlorella (test area), and the number of cells (cells/ml) when cultivation is conducted for a certain period can be compared with the number of cells (cells/ml) in the non-added system cultivated under the same condition (control area), for calculation. Further, cells in the form of callus can also be used. As the callus, a liverwort (*Harchantia polymorpha L.*) callus may be exemplified. When a callus is used, the test substance acting as a plant-activating agent is added to e.g. a sterilized medium for calluses (test area), and the weight of callus when cultivation is conducted for a certain period can be compared with the weight of callus of the non-added system cultivated under the same condition (control area), for calculation. In any case, the concentration of the test substance in the test area is not limited but suitably from 0.1 to 1000 ppm in terms of effective components. Further, it is preferable that the reproduction amounts of cells in the test area and control area are measured per cultivation time and, when the difference between the reproduction amounts of cells is largest, the reproduction amounts of cells are compared to calculate the improved degree in reproduction of green cells.

In the present invention, there is preferable a substance acting as a plant-activating agent which is given in the form of an aqueous solution or an aqueous dispersion in an amount of 0.01 to 5000 ppm, further 0.1 to 1000 ppm and particularly 1 to 500 ppm in terms of an effective (or active) component per a culturing solution of green cells to show not less than 5% of the above-mentioned improved degree in reproduction of green cells. In this case, there is further preferable a substance which shows not less than 5% of the improved degree in reproduction of green cells within 15 days after starting giving at this concentration. When a substance which shows not less than 5% of the improved degree in reproduction of green cells is sprayed in the form of a solid agent such as a granule and a dust formulation, an aqueous solution or an aqueous dispersion of the plant-activating agent, when it is given as an active component in a proportion of 0.001 to 3000 kg, further 0.01 to 1000 kg and particularly 0.05 to 100 kg per 1000 $m^2$ (10 a), it is preferably a substance satisfying at least one of (a), (b), (c), (d) and (e) within 50 days.

In the present invention, there is preferable a substance which has not less than 5% of the improved degree in reproduction of green cells and satisfies at least one, further at least two, more further at least three, particularly at least four, particularly further all five of the following (a), (b), (c), (d) and (e):

(a) Improved degree of SPAD value is not less than 2 points,
(b) Increased amount in weight of the plant (fresh weight or dry weight) is not less than 10%,
(c) Improved degree in leaf-area of a plant is not less than 5%,
(d) Increased amount in concentration of ascorbic acid in the blade part is not less than 5%, and
(e) Decreased degree in concentration of nitrate ion in the blade part is not less than 10%.

The SPAD value (a) is measured as described later, and the improved degree of the SPAD value is preferably not less than 2 points, more preferably not less than 3 points and most preferably not less than 4 points.

[i] Pre-treatment of Plants

First, plural individuals of plants as an object to be measured have been grown under the same conditions. In that time, systems using the substance acting as the plant-activating agent (test areas) and systems using no such substance (control areas) were prepared respectively in plural numbers (preferably, the same number). Usually, this substance is added to a soil or a culturing solution of hydroponics or sprayed onto phylloplanes. Now, the environmental conditions such as temperature, humidity, light intensity and carbon dioxide concentration, conditions such as kind and composition of the soil, growth conditions such as an applied amount of fertilizers given, and growth period are made same in the test area and the control area. Namely, the individuals are grown for a certain period under the same conditions except for the addition of the substance acting as the plant-activating agent. Specific values of the conditions of the pre-treatment may be appropriately determined concerning a kind of the plant, the growth stage and the like. Plants in the test area and control area on which the pre-treatments were thus performed are used for the following measurement of the SPAD value.

[ii] Measurement of the SPAD Value

The SPAD values in the test and control areas grown under the same conditions are measured by Minolta Chlorophyll Meter SPAD 502 (supplied by Minolta Co., Ltd.). This is an apparatus to measure the amount of chlorophyll of plants (leaves) without destruction. Raw leaves are inserted into this apparatus and irradiated with light (stroboscopic emission by a xenon lamp). The transmission light is passed through a filter having 670 nm of the maximum wavelength to be absorbed by chlorophyll and another filter having 750 nm of the non-specific absorption band of a polymer such as protein, the difference in light absorption amounts at both wavelengths is measured by an integrated circuit and converted digitally, and then the value is expressed. The value is indicated in terms of numerical values between zero to 80 (SPAD value). The SPAD value has a high correlation with the chlorophyll content per unit area of a leaf. The following regression formula is satisfied between the value (X) measured by SPAD 502 and the chlorophyll content (Y) (mg/100 cm$^2$) (Shokubutsu Eiyo Jikken Ho (translated as Method for testing nutrition of plants), 2$^{nd}$ press., pp. 366–367 issued on Apr. 20$^{th}$, 1991 by Hakuyu Sha K. K.).

$$Y=0.0996X-0.152$$

Namely, when the SPAD value is higher, the chlorophyll content per unit area of a leaf of a plant is more to show more growth of the plant.

The improved degree of the SPAD value in the present invention is calculated as follows:

Improved degree of the SPAD value=(SPAD value in test area)−(SPAD value in control area).

The measuring time of the SPAD is not limited but only necessitates that the area of a leaf of the plant reaches to an area (about 5 mm×5 mm or more) measurable by a SPAD meter after a treatment with the substance acting as the plant-activating agent. The measurement of the SPAD value is carried out at least 20 times on the same leaf position of a plant treated with the substance acting as the plant-activating agent and of another plant not treated with the substance acting as a plant-activating agent, and the average value thereof is used.

The increased amount in weight of a plant (b) is calculated from fresh weights or dry weights in the test area and control area in which plants have been grown under the same conditions, like in the above-mentioned [i]. The increased amount is preferably not less than 10%, more preferably not less than 15% and most preferably not less than 20%. The weight of a plant is measured as follows. Each and all plants treated with the substance acting as the plant-activating agent (test area) and not treated with the substance acting as the plant-activating agent (control area) are taken out of a cultivation apparatus (e.g. a pot), soil and contaminations adhering to roots are washed away by running water sufficiently, and respective weights are measured (fresh weight). Each of the plants is dried at 70° C. for 5 days and the weight thereof after the drying is measured (dry weight). Increased amounts in weight of plants are calculated respectively by the following manner. Herein, though any of the fresh weight and dry weight may be calculated, the dry weight is preferably calculated for directly reflecting the net weight of an anabolite (assimilate).

Increased amount (%) in weight (fresh weight) of a plant=[(fresh weight in test area−fresh weight in control area)/(fresh weight in control area)]×100

Increased amount (%) in weight (dry weight) of a plant=[(dry weight in test area−dry weight in control area)/(dry weight in control area)]×100

This increased amount in weight of a plant represents increase in substance production and weight and is a direct index of growth of the plant.

The improved degree of leaf-area of a plant (c) is calculated from leaf-area of whole plants in the test area and control area in which plants have been grown in the same conditions, like in the above-mentioned [i]. The improved degree is preferably not less than 5%, more preferably not less than 7% and most preferably not less than 9%. In the present invention, the improved degree of leaf-area is measured using an automatic planimeter AAC-400 model (supplied by Hayashi Denko K. K.). This automatic planimeter is a device to detect, by a photo-electric element, the extent of blockage of scanning beam by a sample. According to this device, the minimum unit is 1 mm$^2$, the maximum display number can be shown up to 99999.99 cm$^2$. A power source switch of the device is turned on, warming up is carried out for at least about 15 minutes, a test plate (with the already-known area of 99.8 cm$^2$) is inserted, and the error range is controlled within 1%. Blade parts of plants in the test area or control area are cut and these cut pieces are used as samples which are inserted at the center position of a film inlet and transported to an outlet, and then the leaf-area is indicated in mm$^2$ unit. It is good to use, as the plant used for measurement, one having little round form or strain in the blade part (for example, tomato, cucumber and spinach). The improved degree of leaf-area is calculated by the following formula from respective leaf-areas in the test area and the control area.

The improved degree of leaf-area (%)=[(leaf-area in test area−leaf-area in control area)/(leaf-area in control area)]×100

It is considerable that a large leaf-area enables a plant to receive an optical energy, to photosynthesize and to produce more substances. The larger improved degree of leaf-area is an index showing more progress of growth of the plant.

The increased amount in concentration of ascorbic acid in the blade part (d) is calculated from concentrations of ascorbic acid in the blade parts of plants in the test area and control area in which plants have been grown under the same conditions, like in the above-mentioned [i]. For measurement of concentration of ascorbic acid in the blade part, RQ flex (supplied by Merk) is used. Ascorbic acid reduces yellow molybdophosphoric acid to produce phosphorus molybdenum blue. In the above-mentioned device, coloring part of this test paper is irradiated with light, and concentration of ascorbic acid in the sample is measured by intensity of the reflected light. A specific measuring method is as follows. The blade parts are cut off from a plant treated with the substance acting as the plant-activating agent (test area) and another plant not treated with the substance acting as the plant-activating agent (control area). In the case of fruit vegetables, the same leaf portion is cut, and in the case of leaf vegetables, the whole plant is cut as the blade part of an object to be measured. Distilled water in 20-fold weight based on weight of the sampled blade part is added, ground in a mortar while cooling with ice, filtrated through double gauzes, and the filtrate is subjected to RQ Flex (supplied by Merk) to measure the concentration of ascorbic acid in the blade part. For suppressing decomposition of ascorbic acid, the obtained filtrate is stored with ice water until the time for measurement. The filtration temperature in measurement is returned to room temperature (15 to 20° C.), and measurement is conducted within 1 hour from generation of the filtrate. Increased amount (%) is calculated by the following formula from concentrations of ascorbic acid in respective blade parts in the test area and the control area.

Increased amount (%) in concentration of ascorbic acid in the blade part=[(concentration of ascorbic acid in blade part in test area−concentration of ascorbic acid in blade part in control area)/(concentration of ascorbic acid in blade part in control area)]×100

High concentration of ascorbic acid in the blade part means that vitamin C content in edible part is large in the case of leaf vegetables and has signification in view of improving the quality. Ascorbic acid is also supposed to perform a role of a scavenger for harmful oxygen radicals generated in plants due to increase in photosynthesis in fruit vegetables and leaf vegetables and is believed to be useful.

The decreased degree in concentration of nitrate ion in the blade part (e) is calculated from concentrations of nitrate ion in the blade parts in the test area and control area in which plants have been grown under the same conditions, like in the above-mentioned [i]. For measurement of concentration of nitrate ion in the blade part, RQ flex (supplied by Merk) is used. Nitric acid in a sample is converted into nitrous acid by a reducing agent, and nitrous acid generated and an aromatic amine react in an acidic buffer, to form a diazonium salt. The diazonium salt azo-couples with N-(1-naphthyl)-ethylenediamine to produce a purple azo compound. In the above-mentioned device, the coloring part of this test paper is irradiated with light, and concentration of nitrate ion in the sample is measured by intensity of the reflected light. A specific measuring method is as follows. The blade parts are cut off from a plant treated with the substance acting as the plant-activating agent (test area) and another plant not treated with the substance acting as the plant-activating agent (control area). In the case of fruit vegetables, the same leaf portion is cut, and in the case of leaf vegetables, the whole plant is cut as the blade part of an object to be measured. Distilled water in 20-fold weight based on weight of the sampled blade part is added, ground in a mortar while cooling with ice, filtrated through double gauzes, and the filtrate is subjected to RQ Flex (supplied by Merk) to measure concentration of ascorbic acid in the blade part. The filtration temperature in measurement is room temperature (15 to 20° C.), and measurement is conducted within 1 hour from generation of the filtrate. Decreased degree (%) is calculated by the following formula from concentrations of nitrate ion in respective blade parts in the test area and the control area.

Decreased degree in concentration of nitrate ion in the blade part (%)=[(concentration of nitrate ion in the blade part in control area−concentration of nitrate ion in the blade part in test area)/ (concentration of nitrate ion in the blade part in control area)]× 100

Nitric acid intaken into human is absorbed in digestive tracts, and then about 25% thereof are re-secreted in saliva and converted into nitrous acid by microorganisms in saliva. When nitrous acid generated in oral cavity is transferred into stomach, a nitroso compound is produced under acidic condition. Reduction in intake of nitric acid which is converted into highly toxic substances such as nitrous acid and nitroso compound is important for safety of food, and a low concentration thereof is significant particularly in the case of agricultural crops.

The plant-activating agent of the present invention preferably comprises the substance having not less than 5% of the standard improved degree in reproduction of chlorella described below.

<Standard Improved Degree in Reproduction of Chlorella>
[i] Cultivation of Chlorella Into a 500-ml Erlenmeyer flask was charged 100 ml of an inorganic salt medium for chlorella (Myers-4NA$_5$; Sorui Jikken Ho (Method for testing algae), $1^{st}$ edition, $1^{st}$ press, P63 to 66 issued on Oct. $23^{rd}$ 1965 by Nankodo K. K.), and the flask was capped with a silicone cap having its ventilative property and placed into an autoclave (at a high temperature, under a high pressure, and a sterilized oven) to sterilize the medium (for 20 minutes). Herein, the substance acting as the plant-activating agent has been added in a concentration of 10 ppm in terms of effective components into a culturing solution in the test area. This substance is not added into the control area. After sterilization, the temperature of the medium is returned to a normal temperature. The number of Chlorella vulgaris which has been sub-cultivated previously is counted under a microscope using a blood cell counting chamber of Thoma, and chlorella is added to the sterilized medium so as to have a concentration of $1.0 \times 10^5$ (cells/ml). These operations are conducted in a clean bench when the sterilized condition is necessary. Cultivation is carried out in a shaking incubator rotating at 110 rpm at 23° C. under continuous illumination (with illuminance of 10 klx.) with carbon dioxide and humidity under natural conditions.

[ii] Measurement for the Number of Chlorella After Cultivation

At $8^{th}$ day (i.e. after 192 hours) from starting cultivation under the above-mentioned conditions, culturing solutions are respectively collected in an amount of 100 μl from the control area and the test area and the number of chlorella is counted by using a blood cell counting chamber of Thoma. This measurement is repeated five times in each area, and the average values ($P_0$, $P_1$) are made as the number of chlorella after cultivation. Thus, an improved degree in reproduction calculated by the formula: $[(P_1-P_0)/P_0] \times 100$ is made as the standard improved degree in reproduction of chlorella of this substance.

A substance having not less than 5% of this standard improved degree in reproduction of chlorella can improve more efficiently activity (or vitality) of many plants, particularly plants used as agricultural crops.

The substance acting as the plant-activating agent of the present invention is more preferably one in which a cultivation time is shorter by 10 to 40% as compared with in the control area until the number of chlorella cultivated according to the conditions and method of [i] in the above-mentioned standard improved degree in reproduction of chlorella reaches $5.0 \times 10^6$ (cells/ml). That is, if cultivation time until the number of chlorella reaches $5.0 \times 10^6$ (cells/ml) by the above-mentioned conditions and method is represented by X in the case of the control area and by Y in the case of the test area, satisfying that $[(X-Y)/X] \times 100 = 10$ to $40(\%)$.

Further, in the substance acting as the plant-activating agent of the present invention, it is more preferable that at least one of the above-mentioned (a), (b), (c), (d) and (e) satisfies the above-mentioned range provided that a measurement is conducted under a standard condition shown below.

<Standard Condition>

A test is carried out in a glass green-house at the temperature of 25° C. under natural light with carbon dioxide and humidity under natural conditions. Kureha Engei Baido (horticultural soil) (fertilizer components: N:P:K= 0.4:1.9:0.6 (g)/soil 1 kg) supplied by Kureha Chemical Industry Co., Ltd. is charged into a cell tray having 50 holes, seeds of tomato "Zuiken" are sown thereon, Kureha Engei Baido is covered thereon to form a thin layer, and the soil is irrigated sufficiently with water to cause germination. Two weeks after germination, seedlings of the tomato are transplanted to a 15-cm (diameter) pot charged with Kureha Engei Baido. The substance acting as the plant-activating agent diluted with a 3000-fold solution of "Otsuka OKF2" supplied by Otsuka Chemical K. K. (fertilizer components: N:P:K:Ca:Mg=14:8:16:6:2), so that a concentration thereof may be 50 ppm in terms of effective components, is allowed to permeate (or penetrate) into the soil seven times every week from $7^{th}$ day after transplantation (at the period for expansion of true leaves) in an amount of about 50 ml per one pot (test area). Further, there is prepared, as the control area, one treated in the same manner only by a 3000-fold solution of "Otsuka OKF2" supplied by Otsuka Chemical K. K. (control area). Third day after completion of the $7^{th}$ treatment, the above-mentioned (a), (b), (c), (d) and (e) are measured. For both of the test area and control area, plural individuals are prepared and three individuals selected arbitrarily are respectively used, and the values of (a), (c), (d) and (e) are calculated using average values thereof. Further, for calculation of (b), other three individuals are used. Herein, the SPAD value is made as an average value obtained respectively by 20-times measurements (data number: 20) for each individual and other values are made respectively as an average value of three individuals (data number: 3).

The substance activating as the plant-activating agent of the present invention includes the following compounds for example.

(1) Fatty Acids or Derivatives Thereof

There may be a monohydric fatty acid represented by the following formula, salts thereof and monohydric fatty acid esters thereof.

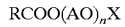
$RCOO(AO)_nX$

In the formula, R represents a hydrogen atom or an alkyl or alkenyl group having 1 to 29 carbon atoms, preferably 5 to 25 carbon atoms and more preferably 13 to 21 carbon atoms, and X represents a hydrogen atom, an alkyl, alkenyl or acyl group having 1 to 30 carbon atoms, or a counter ion. It is preferably a hydrogen atom or an alkyl, alkenyl or acryl group having 14 to 22 carbon atoms. The counter ion may be any of an alkali metal such as sodium and potassium, an alkaline earth metal such as calcium and magnesium, an alkylamine salt such as trimethylamine, triethylamine and a long chain alkylamine salt, an alkanolamine salt such as ethanolamine, and an ammonium salt. It is preferably an alkali metal or an alkaline earth metal. The hydrocarbon group of the monohydric fatty acid and esters thereof may be saturated or unsaturated and is preferably saturated, and may be any of linear, branched and cyclic, is preferably linear or branched, and is more preferably linear. AO represents an oxyalkylene group, is preferably at least one group selected from oxyethylene group, oxypropylene group and oxybutylene group and may be random or block. n represents an average number of moles added and is from zero to 30, preferably from zero to 10, and particularly preferably from zero to 5.

The fatty acid derivatives include sugar ester derivatives such as pentaerythritol fatty acid ester, polyglycerol fatty acid ester, sorbitan fatty acid ester and sucrose fatty acid ester.

In the case of substances having a hydrophilic group and a hydrophobic group among the above-mentioned fatty acid derivatives, its HLB (Hydrophile-Lipophile-Balance) measured by Griffin's method is preferably 10 or less, more preferably 8 or less, and most preferably 5 or less.

(2) Organic Acids or Derivatives Thereof

There may be exemplified hydroxycarboxylic acids and polycarboxylic acids such as citric acid, gluconic acid, malic acid, heptonic acid, oxalic acid, malonic acid, lactic acid, tartaric acid, succinic acid, fumaric acid, maleic acid, adipic acid, glutaric acid and glyceric acid, and salts thereof, for example, potassium salts, sodium salts, ammonium salts, alkanolamine salts and fatty amine salts. Further, there may be exemplified hydroxycarboxylic acid esters or amides such as alkyl citrates and alkyl citric acid amides, polyvalent carboxylates or carboxamides, glyceric acid alkyl esters, glyceric acid alkyl amides.

(3) Lipids and Derivatives Thereof

There may be exemplified animal fats and oils such as tallow, lard, fish oil and whale oil; vegetable fats and oils such as coconut oil, palm oil, palm-stearin oil, castor oil, soybean oil and olive oil; fat and/or oil derivatives such as monoacyl glycerol and diacyl glycerol; phospholipid such as phosphatidylcholines, pohsphatidylserines, phosphatidylethanolamines, sphingomyelin and phosphatidic acid; sphingolipid; glycolipid; terpenoid; and sterols. The derivatives of fat and/or oil includes alkylene oxide adducts to a mixture of fat and/or oil and glycerol, and the average number of moles added of alkylene oxide is from 1 to 30, preferably from 1 to 10, and particularly preferably from 1 to 5.

In the case of substances having a hydrophilic group and a hydrophobic group among the above-mentioned lipid derivatives, its HLB measured by Griffin's method is preferably 10 or less, more preferably 8 or less, and most preferably 5 or less.

(4) Alcohols or Derivatives Thereof

There may be exemplified monohydric alcohol and derivatives thereof or polyhydric alcohols and derivatives thereof.

(4-1) Monohydric Alcohols and Derivatives Thereof

There may be exemplified a compound represented by the following formula.

$RO(AO)_nX$

In the formula, R represents an alkyl or alkenyl group having 1 to 30 carbon atoms, preferably 12 to 26 carbon atoms and particularly preferably 14 to 22 carbon atoms, may be saturated or unsaturated, and may be any of linear, branched or cyclic. There is preferably a linear or branched one, and particularly preferably a linear alkyl group. X represents a hydrogen atom or an alkyl or alkenyl group having 1 to 30 carbon atoms, preferably 12 to 26 carbon atoms and particularly preferably 14 to 22 carbon atom, may be saturated or unsaturated, and may be any of linear, branched or cyclic. It is preferably a linear or branched one, and particularly preferably a linear alkyl group. AO represents an oxyalkylene group, is preferably at least one group selected from oxyethylene group, oxypropylene group and oxybutylene group, and may be random or block. n represents an average number of moles added and is from zero to 30, preferably from zero to 10, and particularly preferably from zero to 5.

Specific examples of the monohydric alcohol and derivatives thereof include monohydric alcohols such as methanol, ethanol, propanol, butanol, lauryl alcohol, myristyl alcohol, cetyl alcohol, stearyl alcohol, eicosanol, behenyl alcohol, phytol and oleyl alcohol; polyoxyalkylene monoalkyl ethers such as POE (abbreviated for polyoxyethylene) (n=1) stearyl ether and POE (n=3) cetyl ether; dialkyl ethers such as distearyl ether and stearyl cetyl ether; polyoxyalkylene dialkyl ethers.

(4-2) Polyhydric Alcohols and Derivatives Thereof

The examples of the polyhydric alcohol include glycols such as ethylene glycol, diethylene glycol and polyethylene glycol; sugar alcohols such as sorbitol, mannitol and glucose; erythritol, pentaerythritol, pentitol and glycerol or derivatives thereof.

Further, there may be exemplified a condensed product of the polyhydric alcohol and a condensed product of the monohydric alcohol and the polyhydric alcohol. The condensed product of the polyhydric alcohol includes polyglycerol of the following formula and derivatives thereof.

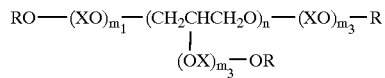

In the formula, n represents a number selected from 2 to 50, R is a hydrogen atom or an acyl group having 2 to 31 carbon atoms, X represents an alkylene group having 2 to 4 carbon atoms, and each of $m_1$, $m_2$ and $m_3$ represents a number selected from zero to 30.

The condensed product of the monohydric alcohol and the polyhydric alcohol includes alkyl glyceryl ethers such as batyl alcohol, isostearyl glyceryl ether and behenyl glyceryl ether. The condensed product of the monohydric alcohol and the sugar or sugar alcohol includes alkyl polyglycosides such as decyl polyglucoside and stearyl polyglucoside.

Further, there may be exemplified polyhydric alcohol fatty acid amides such as N-lauroyl N-methylglucamide and N-stearoyl N-methylglucamide.

Furthermore, alkylene oxide adducts of these polyhydric alcohols and derivatives thereof may be exemplified. The alkylene oxide is preferably at least one selected from ethylene oxide, propylene oxide and butylene oxide, and may be added at random or in block. The average number of moles added is from zero to 30, preferably from zero to 10, and particularly preferably from zero to 5 moles.

In the case of substances having a hydrophilic group and a hydrophobic group among the above-mentioned alcohol derivatives, its HLB measured by Griffin's method is preferably 10 or less, more preferably 8 or less, and most particularly preferably 5 or less.

(5) Amines or Derivatives Thereof

There may be exemplified amines including a primary, secondary or tertiary lower amine having a $C_{1-7}$ hydrocarbon group, preferably an alkyl group, such as monomethylamine, dimethylamine and trimethylamine and including a polyamine such as a primary, secondary or tertiary long chain amine, diamine or triamine having a $C_{8-30}$ hydrocarbon group, preferably an alkyl group, or a salt thereof. The derivative includes a quaternary ammonium salt, choline or a salt thereof, and a fatty acid salt of choline.

(6) Amino Acids or Derivatives Thereof

There may be exemplified D,L-amino acids such as aspartic acid, threonine, serine, glutamic acid, glutamine, proline, glycine, alanine, cysteine, valine, methionine, isoleucine, leucine, tyrosine, phenylalanine, lysine, histidine, tryptophane and arginine. Further, there may be exemplified derivatives of ornithine, creatine, hydroxyproline and acylated glutamine.

(7) Proteins or Derivatives Thereof

There may be exemplified peptides or polypeptides which are composed of connected amino acids and which include glutathione and oxytocin, proteins and glycoproteins such as casein, keratin, hemoglobin, albumin and collagen, enzymes which catalyze a vital reaction.

(8) Nucleic Acids or Derivatives Thereof

There may be exemplified ribonucleic acids, deoxyribonucleic acids, decomposed products thereof, nucleoside phosphates such as adenosine triphosphate, and nucleotides which are constituent units thereof.

(9) Terpenes or Derivatives Thereof

There may be exemplified terpenes such as orange oil, turpentine oil, peppermint oil, eucalyptus oil, d-camphor, dl-camphor, 1-menthol, dl-menthol and thymol or derivatives thereof.

(A) Natural Extracts

There may be exemplified natural extracts such as hinokitiol, chitin, chitosan, chlorella-decomposed products and wood vinegar.

(B) Fermentation Products

There may be exemplified fermentation products obtained by amino acid fermentation, mixed organic acid fermentation, glycerol fermentation and penicillin fermentation.

(C) Fermentation Residues

There may be exemplified residues in the above-mentioned fermentation (B) and microorganism cultivation.

(I) Vitamins

There may be exemplified water-soluble vitamins such as thiamine, riboflavin, nicotinic acid, pantothenic acid, pyridoxine, biotin, folic acid, vitamin $B_{12}$ and ascorbic acid, or coenzymes thereof, and oil-soluble vitamins such as vitamins A, D, E and K.

Among them, substances selected from the above-mentioned (1), (2), (3) and (4) are preferable, substances selected from the above-mentioned (1), (3) and (4) are more preferable, and substances selected from the above-mentioned (4) are most preferable.

The plant-activating agent of the present invention may comprise the above-mentioned substance of the present invention alone or may comprise other components. The components include surfactants and chelating agents. The surfactants and chelating agents may also satisfy the above-mentioned improved degree in reproduction of green cells, the conditions (a), (b), (c), (d) and (e), and the standard improved degree in reproduction of chlorella.

The surfactant is preferably at lest one selected from nonionic surfactants, cationic surfactants, amphoteric surfactants and anionic surfactants.

Examples of the nonionic surfactant include sorbitan fatty acid esters, polyoxyalkylene sorbitan fatty acid esters, polyoxyalkylene fatty acid esters, glycerol fatty acid esters, polyoxyalkylene glycerol fatty acid esters, polyglycerol fatty acid esters, polyoxyalkylene polyglycerol fatty acid esters, sucrose fatty acid esters, resin acid esters, polyoxyalkylene resin acid esters, polyoxyalkylene alkyl ethers, polyoxyalkylene alkylphenyl ethers, alkyl(poly)glycosides and polyoxyalkylene alkyl(poly)glycosides. They preferably include an ether group-containing nonionic surfactants having no nitrogen atom and an ester group-containing nonionic surfactant.

Examples of the anionic surfactants include carboxylic, sulfonic, sulfuric ester group-containing and phosphoric ester group-containing surfactants. The carboxylic and phosphate group-containing surfactants are preferable. Examples of the carboxylic surfactants include fatty acids having 6 to 30 carbon atoms or salts thereof, polyhydric carboxylic acid salts, polyoxyalkylene alkyl ether carboxylic acid salts, polyoxyalkylene alkylamide ether carboxylic acid salts, rhodinic acid salts, dimer acid salts, polymer acid salts and tall oil fatty acid salts. Examples of the sulfonic surfactants include alkylbenzensulfonates, alkylsulfonates, alkylnaphthalenesulfonates, naphthalenesulfonates, diphenyl ether sulfonic acid salts, condensates of alkylnaphthalenesulfonates and condensates of naphthalenesulfonates. Examples of the sulfuric ester group-containing surfactant include alkylsulfates, polyoxyalkylene alkylsulfates, polyoxyalkylene alkyl phenyl ether surfuric acid salts, tristyrenized phenol sulfuric acid salts, polyoxyalkylene distyrenized phenol sulfuric acid ester salts and alkylpolyglycoside sulfuric acid salts. Examples of the phosphoric acid group-containing surfactant include alkylphosphoric acid ester salts, alkylphenylphosphoric acid ester salts, polyoxyalkylene alkylphosphoric acid ester salts and polyoxyalkylene alkylphenylphosphoric acid ester salts. Examples of the salts include salts of metals (such as Na, K, Ca, Mg and Zn), ammonium salts, alkanolamine salts and aliphatic amine salts.

Examples of the amphoteric surfactant include amino acid group-containing, betaine-containing, imidazoline-containing, amine oxide-containing surfactants. Examples of the amino acid group-containing surfactants include acylamino acid salts, acylsarcosinic acid salts, acyloylmethylaminopropionic acid salts, alkylaminopropionic acid salts and acylamide ethylhydroxyethylmethylcarboxylic acid salts. Examples of the betaine group-surfactants include alkyldimethylbetaine, alkylhydroxyethylbetaine, acylamide propylhydroxypropylammonia sulfobetaine, acylamide propylhydroxypropylammonia sulfobetaine and ricinoleic acid amide propyl dimethylcarboxy methylammonia betaine. Examples the imidazoline group-containing surfactants include alkylcarboxy methylhydroxy ethylimidazolinium betaine and alkylethoxy carboxy methylimdazolinium betaine. Examples of the amine oxide group-containing surfactants include alkyldimethylamine oxide, alkyldiethanolamine oxide and alkylamidepropylamine oxide.

One kind of the above-mentioned surfactants may be used, and a mixture of two or more kinds thereof may be used. In order to solubilize and disperse uniformly effective components of the plant-activating agent, the above-mentioned surfactant is desirably a highly hydrophilic surfactant. In this surfactant, its HLB measured by Griffin's method is preferably not less than 10 and more preferably not less than 12. When these surfactants contain a polyoxyalkylene group, it is preferably polyoxyethylene group and the average number of moles added may be mentioned as from 1 to 50. The average number of moles added is more preferably from 5 to 30 and most preferably from 10 to 30.

The surfactant is preferably at least one selected from ester group-containing nonionic surfactants, ether group-containing nonionic surfactants having no nitrogen atom, amphoteric surfactants, carboxylic anionic surfactants and phosphoric acid group-containing anionic surfactants. There is particularly preferable at least one selected from ester group-containing nonionic surfactants and ether group-containing nonionic surfactants having no nitrogen atom. In the plant-activating agent of the present invention, it is preferable that the ratio by weight of the surfactants to the active components (substances having 5% or more of the improved degree in reproduction of green cells in the present invention), namely the surfactants/the effective components, is preferably from 0.01 to 100, more preferably from 0.05 to 50 and most preferably from 0.1 to 30 in view of efficiently permeating the active components into plants.

The chelating agents may be aminopolycarboxylic acid group-containing chelating agents, aromatic or aliphatic carboxylic acid group-containing chelating agents, amino acid group-containing chelating agents, ether polycarboxylic acid group-containing chelating agent, phosphonic acid group-containing chelating agent (such as iminodimethylphosphonic acid (IDP) and alkyldiphosphonic acid (ADPA)) or dimethylglyoxime (DG). These may be in the form of an acid itself or a salt with sodium, potassium or ammonium.

As the aminopolycarboxylic acid group-containing chelating agent, there can be used all of
a) compounds represented by $RNX_2$,
b) compounds represented by $NX_3$,
c) compounds represented by R—NX—$CH_2CH_2$—NX—R,
d) compounds represented by R—NX—$CH_2CH_2$—$NX_2$ and
e) compounds represented by $X_2N$—R'—$NX_2$ and compounds represented thereby in which X is 4 or more. In the above-described formulae, X represents —$CH_2COOH$ or —$CH_2CH_2COOH$, R represents a hydrogen atom, an alkyl group, a hydroxy group, a hydroxyalkyl group or a substituent realizing this kind of publicly known chelating compounds, and R' represents an alkylene group, a cycloalkylene group or a group realizing this kind of publicly known chelating compounds. Typical examples thereof include ethylenediaminetetraacetic acid (EDTA), cyclohexanediaminetetraacetic acid (CDTA), nitrilotriacetic acid (NTA), iminodiacetic acid (IDA), N-(2-hydroxyethyl)imiodiacetic acid (HIMDA), diethylenetriaminepentaacetic acid (DTPA), N-(2-hydroxyethyl) ethylenediaminetriacetic acid (EDTA-OH) and glycol ether diaminetetraacetic acid (GEDTA) and salts thereof.

The aromatic or aliphatic carboxylic acid group-containing chelating agents include citric acid, oxalic acid, glycolic acid, pyruvic acid or anthranilic acid and salts thereof.

The amino acid group-containing chelating agents may be glycine, serine, alanine, lysine, cystine, cysteine, ethionine, tyrosine or methionine and salts and derivatives thereof. Further, the ether polycarboxylic acid group-containing chelating agent which can be used in the present invention may be compounds represented by the following formula and analogous compounds and salts (particularly, Na salt, etc.) thereof, for instance.

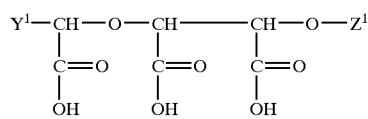

In the formula, there means that

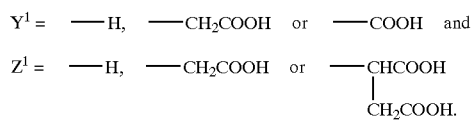

The form of the plant-activating agent in the present invention may be any one of liquid, flowable, paste, wettable powder, granule, dust formulation and tablet. When the agent is diluted with water to be used, the diluted one as an aqueous solution, aqueous dispersion or emulsion is generally sprayed onto phylloplanes or roots of plants in a concentration of the effective components of the plant-activating agent of 0.01 to 5000 ppm.

The present invention provides a method of improving activity of a plant, comprising supplying the above-mentioned plant-activating agent of the present invention to the plant. The method of supplying the plant-activating agent in the present invention to a plant, various techniques may be used. For example, it includes a method of giving directly a dust formulation or a granule as a solid fertilizer such as a chemical fertilizer, a method of spraying a diluted aqueous solution directly on phylloplanes, stems or fruits of a plant, a method of injecting a diluted aqueous solution into soil, and a method of supplying to dilute and to mix into a liquid for hydroponics and a supplying water which are contacted with roots, such as hydroponics and a rock wool.

Plants, which can be treated with the plant-activating agent of the present invention, may be fruit vegetables such as a cucumber, a pumpkin, a watermelon-plant, a melon, a tomato, an eggplant, a green pepper, a strawberry, an okra, kidney beans in a pod, a broad bean, a pea, green soybeans in a pod and a corn; leaf vegetables such as a Chinese cabbage, greens for pickling, a *Brassica campestris* (a Chinese spinach-like green vegetable), a cabbage, a cauliflower, a broccoli, a Brussels sprout, an onion, a Welsh onion, a garlic, a scallion, a leek, an asparagus, a lettuce, a green for salad (which is called Saladana in Japan), a celery, a spinach, a crown daisy, a parsley, a trefoil (which is called Mitsuba in Japan and is useful as herb), a dropwort, an udo (which is an *Aralia cordata*), a Japanese ginger, a Japanese butterbur and a labiate; and root vegetables such as a radish, a turnip, a burdock, a carrot, a potato, a taro, a sweet potato, a yam, a ginger-plant (which is called Shoga in Japan) and a lotus root. Besides, the plant-activating agent may be used for a rice-plant, a barley, a wheat or a group thereof, and petalous-plants.

Advantageous Effect of the Invention

Treated by the plant-activating agent of the present invention in an appropriate concentration, the activity of a plant can be efficiently improved without a chemical injury to the plant. Thus, the plant-activating agent can be used for various farm products. Furthermore, the present invention causes improvement seen in plant-growth, such as promotion of taking root of a plant, increase in weight, increase of SPAD value, increase of leaf-area, increase in concentration of ascorbic acid in the blade part and decrease in concentration of nitrate ion in the blade.

EXAMPLES

Example 1

In the above-mentioned cultivation conditions and method for the standard improved degree in reproduction of chlorella, there was measured the improved degree in reproduction of green cells at $8^{th}$ day (after 192 hours) after starting the cultivation. However, concentrations of substances added to the culturing solution in the test area are shown in Table 1. The results are shown in Table 1. The results in Table 1 are relative values when the value in the control area is made as 100. The standard improved degree in reproduction of chlorella is shown except the inventive products 1-6, 1-12 and 1-15.

TABLE 1

|  |  |  | Plant-activating agent | | Test result Improved degree in |
|---|---|---|---|---|---|
|  | Test No. | Blended component | | Concentration (ppm) | reproduction of green cells |
| Inventive product | 1-1 | Stearic acid | | 10 | 160 |
|  | 1-2 | Palmitic acid | | 10 | 130 |
|  | 1-3 | Sodium isethionate | | 10 | 120 |
|  | 1-4 | Sodium glutamate | | 10 | 110 |
|  | 1-5 | Stearyl alcohol | | 10 | 170 |
|  | 1-6 | Behenyl alcohol POE(20) sorbitan oleate | | 10 5 | 136 |
|  | 1-7 | Citric acid monostearyl ester | | 10 | 135 |
|  | 1-8 | Citric acid monooleyl axnide | | 10 | 148 |

TABLE 1-continued

|  | Test No. | Plant-activating agent Blended component | Concentration (ppm) | Test result Improved degree in reproduction of green cells |
|---|---|---|---|---|
|  | 1-9 | Distearyl ether | 10 | 160 |
|  | 1-10 | Stearyl stearate | 10 | 152 |
|  | 1-11 | POE(1) stearyl ether | 10 | 160 |
|  | 1-12 | Tallow | 10 | 120 |
|  |  | Sodium succinate | 20 |  |
|  | 1-13 | Stearic acid diglyceride | 10 | 140 |
|  | 1-14 | Pentaerythritol monostearate | 10 | 110 |
|  | 1-15 | Batyl alcohol | 10 | 160 |
|  |  | EDTA-4Na | 4 |  |
|  | 1-16 | Palm oil | 10 | 115 |
|  | 1-17 | Glyceric acid stearyl ester | 10 | 132 |
|  | 1-18 | Vitamin $B_6$ | 10 | 118 |
|  | 1-19 | Vitamin $B_{12}$ | 10 | 110 |
|  | 1-20 | L-leucine | 10 | 144 |
|  | 1-21 | Tartaric acid | 10 | 110 |
|  | 1-22 | Tallow fatty acid choline | 10 | 126 |
|  | 1-23 | Stearic acid monoglyceride | 10 | 140 |
|  | 1-24 | Biotin | 10 | 112 |
| Comparative product | 1-1 | POE(20) sorbitan oleate | 10 | 85 |
|  | 1-2 | Sodium succinate | 10 | 90 |
|  | 1-3 | EDTA-4Na | 10 | 92 |
| Control area |  | Only the culturing solution | — | 100 |

Example 2

In the above-mentioned cultivation conditions and method for the standard improved degree in reproduction of chlorella, there was measured the improved degree in reproduction of green cells at $8^{th}$ day (after 192 hours) after starting the cultivation. However, concentrations of substances added to the culturing solution in the test area are shown in Table 2. The results are shown in Table 2. The results in Table 2 are relative values when the value in the control area is made as 100.

TABLE 2

|  | Test No. | Plant-activating agent Blended component | Concentration (ppm) | Test result Improved degree in reproduction of green cells |
|---|---|---|---|---|
| Inventive product | 2-1 | Stearyl acid | 50 | 156 |
|  | 2-2 | Palmitic acid | 30 | 140 |
|  | 2-3 | Sodium isethionate | 100 | 126 |
|  | 2-4 | Sodium glutamate | 50 | 115 |
|  | 2-5 | Behenyl alcohol | 50 | 130 |
|  |  | POE(20) sorbitan oleate | 5 |  |
|  | 2-6 | Citric acid monooleyl amide | 20 | 140 |
|  | 2-7 | Distearyl ether | 50 | 165 |
|  | 2-8 | Stearyl stearate | 50 | 142 |
|  | 2-9 | POE(1) stearyl ether | 50 | 153 |
|  | 2-10 | Tallow | 50 | 124 |
|  |  | Sodium succinate | 20 |  |
|  | 2-11 | Stearic acid diglyceride | 50 | 136 |
|  | 2-12 | Pentaerythritol monostearate | 50 | 108 |
|  | 2-13 | Batyl alcohol | 20 | 150 |
|  |  | EDTA-4Na | 4 |  |
|  | 2-14 | Palm oil | 50 | 125 |
|  | 2-15 | Glyceric acid stearyl ester | 20 | 140 |
|  | 2-16 | Vitamin $B_6$ | 50 | 122 |
|  | 2-17 | Vitamin $B_{12}$ | 50 | 118 |
|  | 2-18 | L-leucine | 50 | 156 |
|  | 2-19 | Tallow fatty acid choline | 30 | 132 |
|  | 2-20 | Biotin | 5 | 115 |

TABLE 2-continued

|  |  | Plant-activating agent | | Test result Improved degree in |
|---|---|---|---|---|
| Test No. | | Blended component | Concentration (ppm) | reproduction of green cells |
| Comparative | 2-1 | POE(20) sorbitan oleate | 50 | 80 |
| product | 2-2 | Sodium succinate | 20 | 92 |
| | 2-3 | EDTA-4Na | 5 | 90 |
| Control area | | Only the culturing solution | — | 100 |

Example 3
<Measurement of SPAD Value etc.>
(3-1 Test Plant)

Species: tomato "Momotato"
Vessel for cultivation:
a cell tray having 50 holes for germination
a 15-cm (diameter) pot for cultivation
Used soil: Kureha Engei Baido (supplied by Kureha Chemical Industry Co., Ltd.) [the fertilizer components: N:P:K=0.4:1.9:0.6 (g/soil 1 kg)]
(3-2 Cultivation Condition and Measurement)

In the above-mentioned conditions, in a glass green-house at the temperature of 25° C. under natural light with carbon dioxide and humidity under natural conditions, seeds were sown into a cell tray having 50 holes. Two weeks after germination, seedlings thereof were transplanted to the pot. With the plant-activating agent-mixed solution comprising the plant-activating agent as shown in Tables 3 and 4 and a 3000-fold diluted solution of "Otsuka OKF2" (supplied by Otsuka Chemical K. K.) as a fertilizer component, the soil was treated seven times in total every week from seven days after the transplantation. Concentrations of the plant-activating agent in the mixed solutions are shown in Tables 3 and 4. The balance therein is water. The soil was permeated with the treated amount of about 50 ml per one pot. Third day after completion of the $7^{th}$ treatment, the SPAD value, the improved degree of leaf-area, the increased amount in concentration of ascorbic acid in the blade part and the decreased degree in concentration of nitrate ion in the blade part were measured by the above-mentioned methods. For both of the test area and control area, plural individuals were prepared and three individuals selected arbitrarily were used for the measurement. The results are shown in Tables 3 and 4, and the SPAD value is an average value obtained respectively for the 3 individuals by 20-times measurements (data number: 60), and other values are an average value of the 3 individuals (data number: 3). Besides, for 3 individuals other than these, $3^{rd}$ day after completion of the $7^{th}$ treatment, the increased amount in plant-weight (dry weight) was measured by the above-mentioned method. The results are also shown in Tables 3 and 4. In Tables 3 and 4, the values except the SPAD value are relative values as compared with that in the control area.

TABLE 3

| Test No. | Plant-activating agent | | SPAD value (point) | Dry weight of plant (%) | Leaf-area (%) | Concentration of ascorbic acid in the blade part (%) | Concentration of nitrate ion in the blade part (%) |
|---|---|---|---|---|---|---|---|
| | Blended component | Concentration (ppm) | | | | | |
| Inventive product | | | | | | | |
| 3-1 | Stearic acid | 50 | 37 | 115 | 108 | 130 | 78 |
| | POE(20) sorbitan monooleate | 150 | | | | | |
| 3-2 | Palmitic acid | 50 | 36.9 | 114 | 105 | 122 | 82 |
| | POE(6) sorbitan monooleate | 150 | | | | | |
| 3-3 | Sodium isetionate | 50 | 37.2 | 112 | 108 | 119 | 85 |
| | POE(20) sorbitan monostearate | 150 | | | | | |
| 3-4 | Sodium glutamate | 50 | 36.3 | 118 | 110 | 120 | 86 |
| | POE(20) sorbitan tristearate | 150 | | | | | |
| 3-5 | Stearyl alcohol | 50 | 38.6 | 128 | 121 | 149 | 72 |
| | POE(20) sorbitan monooleate | 150 | | | | | |
| 3-6 | Behenyl alcohol | 50 | 37.3 | 116 | 107 | 124 | 84 |
| | POE(10) monolaurate | 150 | | | | | |
| 3-7 | Citric acid monostearate | 50 | 37.9 | 120 | 115 | 135 | 78 |
| | Sorbitan monooleate | 150 | | | | | |
| 3-8 | Citric acid monooleyl amide | 50 | 38.8 | 122 | 118 | 122 | 79 |
| | POE(6) sorbitan monolaurate | 150 | | | | | |
| 3-9 | Distearyl ether | 50 | 38.1 | 120 | 112 | 134 | 79 |

TABLE 3-continued

| Test No. | Plant-activating agent Blended component | Concentration (ppm) | SPAD value (point) | Dry weight of plant (%) | Leaf-area (%) | Concentration of ascorbic acid in the blade part (%) | Concentration of nitrate ion in the blade part (%) |
|---|---|---|---|---|---|---|---|
| 3-10 | Stearyl stearate | 50 | 37.4 | 118 | 109 | 118 | 78 |
|  | POE(30) sorbit tetraoleate | 150 |  |  |  |  |  |
| Control area | Only the fertilizer components | — | 34.3 | 100 | 100 | 100 | 100 |

TABLE 4

| Test No. | Plant-activating agent Blended component | Concentration (ppm) | SPAD value (point) | Dry weight of plant (%) | Leaf-area (%) | Concentration of ascorbic acid in the blade part (%) | Concentration of nitrate ion in the blade part (%) |
|---|---|---|---|---|---|---|---|
| Inventive Product |  |  |  |  |  |  |  |
| 3-11 | POE(1) stearyl ether | 50 | 37 | 114 | 108 | 116 | 89 |
| 3-12 | Tallow | 50 | 36.3 | 111 | 109 | 117 | 80 |
|  | POE(40) sorbit tetraoleate | 150 |  |  |  |  |  |
| 3-13 | Stearic acid diglyceride | 50 | 38 | 112 | 110 | 128 | 82 |
|  | POE(20) hardened (or hydrogenated) castor oil | 150 |  |  |  |  |  |
| 3-14 | Pentaerythritol monostearate | 50 | 37.1 | 111 | 109 | 120 | 81 |
|  | Sodium POE(3) lauryl ether sulfate | 150 |  |  |  |  |  |
| 3-15 | Batyl alcohol | 100 | 37.5 | 120 | 115 | 129 | 80 |
|  | EDTA-4Na | 20 |  |  |  |  |  |
| 3-16 | Hexaglycerol monostearate | 100 | 36.8 | 115 | 108 | 119 | 84 |
| 3-17 | Palm oil | 50 | 38.0 | 121 | 110 | 122 | 82 |
| Comparative product |  |  |  |  |  |  |  |
| 3-1 | POE(20) sorbitan monooleate | 150 | 35.1 | 103 | 102 | 100 | 99 |
| 3-2 | POE(8) oleyl ether | 150 | 35.0 | 101 | 103 | 102 | 98 |
| 3-3 | POE(6) sorbitan monolaurate | 150 | 35.0 | 100 | 102 | 101 | 99 |
| 3-4 | Sodium POE(3) lauryl ether sulfate | 150 | 34.9 | 100 | 100 | 101 | 100 |
| 3-5 | POE(20) sorbitan tristearate O2y | 150 | 35.1 | 101 | 101 | 102 | 98 |
| Control nly the fertilizer components area | — |  | 34.3 | 100 | 100 | 100 | 100 |

POE is an abbreviation for polyoxyethylene, and the number in parentheses indicates an average number of moles added of ethylene oxide (this is the same hereinafter).

Example 4
<Measurement of SPAD Value etc.>
(4-1 Test Plant)
Species: spinach "Esper"
Vessel for cultivation: a 18-cm (diameter) pot for cultivation
Used soil: Kureha Engei Baido (supplied by Kureha Chemical Industry Co., Ltd.) [the fertilizer components: N:P:K=0.4:1.9:0.6 (g/soil 1 kg)]
(4-2 Cultivation Condition and Measurement)
In the above-mentioned conditions, in a glass green-house at the temperature of 25° C. under natural light with carbon dioxide and humidity under natural conditions, Kureha Engei Baido was used in an amount of 1.3 L (1.5 kg) per one pot, and seeds were sown thereon. From 12 days after seeding, the treatments were initiated. With the plant-activating agents as shown in Tables 5 and 6, the soil was treated five times in total every week. The concentrations of the plant-activating agents are shown in Tables 5 and 6. The balance therein is water. The soil was permeated with the treated amount of about 150 ml per one pot. Third day after completion of the $5^{th}$ treatment, the SPAD value, the improved degree of leaf-area, the increased amount in concentration of ascorbic acid in the blade part and the decreased degree in concentration of nitrate ion in the blade part were measured by the above-mentioned methods. For both of the test area and control area, plural individuals were prepared and three individuals selected arbitrarily were used for the measurement. The results are shown in Tables 5 and 6, and the SPAD value is an average value obtained respectively for the 3 individuals by 20-times measurements (data number: 60), and other values are an average value of the 3 individuals (data number: 3). Besides, for 3 individuals other than these, $3^{rd}$ day after completion of the $5^{th}$ treatment, the increased amount in plant-weight (dry weight) was measured by the above-mentioned method. These results are also shown in Tables 5 and 6. In Tables 5 and 6, the values except the SPAD value are relative values as compared with that in the control area.

sterilization, the temperature of the medium was returned to a normal temperature. 2 ml of liverwort callus cells under a steady state, which had been sub-cultivated previously, were sucked up by a 2-ml Komagome pipette (measuring pipet) and incubated to the sterilized medium. These operations are

TABLE 5

| Test No. | Plant-activating agent Blended component | Concentration (ppm) | SPAD value (point) | Dry weight of plant (%) | Leaf-area (%) | Concentration of ascorbic acid in the blade part (%) | Concentration of nitrate ion in the blade part (%) |
|---|---|---|---|---|---|---|---|
| Inventive product | | | | | | | |
| 4-1 | Vitamin B$_6$ | 50 | 46.5 | 115 | 108 | 109 | 83 |
| | POE(20) sorbitan monooleate | 150 | | | | | |
| 4-2 | Vitamin B$_{12}$ | 50 | 45.9 | 115 | 108 | 111 | 85 |
| 4-3 | Sodium isethionate | 50 | 47.0 | 112 | 107 | 114 | 88 |
| | POE(20) sorbitan monostearate | 150 | | | | | |
| 4-4 | Sodium glutamate | 50 | 46.8 | 115 | 110 | 109 | 87 |
| | POE(20) sorbitan tristearate | 150 | | | | | |
| 4-5 | Stearyl alcohol | 50 | 49.2 | 125 | 112 | 106 | 70 |
| | POE(20) sorbitan monooleate | 150 | | | | | |
| 4-6 | L-leucine | 50 | 49.0 | 118 | 110 | 113 | 85 |
| 4-7 | Citric acid monostearate | 50 | 50.2 | 120 | 110 | 117 | 75 |
| | Sorbitan monooleate | 150 | | | | | |
| 4-8 | Citric acid monooleyl amide | 50 | 48.5 | 119 | 109 | 112 | 76 |
| | POE(6) sorbitan monolaurate | 150 | | | | | |
| Control area | Water | — | 43.1 | 100 | 100 | 100 | 100 |

TABLE 6

| Test No. | Plant-activating agent Blended component | Concentration (ppm) | SPAD value (point) | Dry weight of plant (%) | Leaf-area (%) | Concentration of ascorbic acid in the blade part (%) | Concentration of nitrate ion in the blade part (%) |
|---|---|---|---|---|---|---|---|
| Inventive product | | | | | | | |
| 4-9 | Distearyl ether | 50 | 49.5 | 116 | 111 | 120 | 73 |
| 4-10 | Tartaric acid | 50 | 47.8 | 118 | 108 | 108 | 84 |
| | POE(30) sorbit tetraoleate | 150 | | | | | |
| 4-11 | POE(1) stearyl ether | 50 | 46.8 | 112 | 110 | 114 | 86 |
| 4-12 | Tallow fatty acid choline | 50 | 45.8 | 112 | 109 | 112 | 86 |
| | POE(40) sorbit tetraoleate | 150 | | | | | |
| 4-13 | Stearic acid monoglyceride | 50 | 46.8 | 116 | 110 | 122 | 78 |
| | POE(20) hardened castor oil | 150 | | | | | |
| 4-14 | Biotin | 50 | 47.6 | 119 | 109 | 109 | 77 |
| | Sodium POE(3) lauryl ether sulfate | 150 | | | | | |
| Comparative product | | | | | | | |
| 4-1 | POE(20) sorbitan monooleate | 150 | 43.5 | 101 | 96 | 98 | 100 |
| 4-2 | Sodium POE(3) lauryl ether sulfate | 150 | 42.5 | 98 | 95 | 95 | 101 |
| Control area | Water | — | 43.1 | 100 | 100 | 100 | 100 |

Example 5

100 ml of the medium (MSK2 medium) for liverworts were placed into a 500-ml Erlenmeyer flask, and the flask was capped with a silicon cap having its ventilative property and placed into an autoclave (at a high temperature, under a high pressure, and a sterilized oven) to sterilize the medium (for 20 minutes). Herein, the substance acting as the plant-activating agent was added in a concentration shown in Table 7 into a culturing solution in the test area. After conducted in a clean bench when sterilized condition is necessary. Cultivation is carried out in a shaking incubator rotating at 110 rpm at 23° C. under continuous illumination (with illuminance of 10 klx.) with carbon dioxide and humidity under natural conditions. Tenth day (after 240 hours) after starting the cultivation, the whole culturing solution in each area was filtrated under suction, and the fresh weight (raw weight) (g) of the callus cell was measured. This was made as the amount in reproduction of green cells, and the improved degree in reproduction of green cells was measured by the above-described formula. The results are shown in Table 7. The results in Table 7 are relative values when that in the control area is made as 100.

TABLE 7

| | | Plant-activating agent | | Test result Improved degree in |
|---|---|---|---|---|
| Test No. | | Blended component | Concentration (ppm) | reproduction of green cells |
| Inventive product | 5-1 | Stearic acid | 50 | 120 |
| | 5-2 | Palmitic acid | 30 | 110 |
| | 5-3 | Sodium isethionate | 100 | 115 |
| | 5-4 | Sodium glutamate | 50 | 105 |
| | 5-5 | Stearyl alcohol | 10 | 140 |
| | 5-6 | Behenylalcohol | 50 | 130 |
| | | POE(20) sorbitan oleate | 5 | |
| | 5-7 | Citric acid monostearate | 10 | 135 |
| | 5-8 | Citric acid oleyl amide | 20 | 125 |
| | 5-9 | Distearyl ether | 50 | 135 |
| | 5-10 | Stearyl sterate | 50 | 125 |
| | 5-11 | POE(1) stearyl ether | 10 | 133 |
| | 5-12 | Tallow | 50 | 124 |
| | | Sodium succinate | 20 | |
| | 5-13 | Stearic acid diglyceride | 50 | 126 |
| | 5-14 | Pentaerythritol monostearate | 50 | 108 |
| | 5-15 | Batyl alcohol | 20 | 128 |
| | | EDTA-4Na | 4 | |
| | 5-16 | Palm oil | 50 | 111 |
| | 5-17 | Glyceric acid stearyl ester | 20 | 108 |
| | 5-18 | Vitamin $B_6$ | 50 | 107 |
| | 5-19 | Vitamin $B_{12}$ | 20 | 108 |
| | 5-20 | L-leucine | 5 | 110 |
| | 5-21 | Tartaric acid | 10 | 110 |
| | 5-22 | Tallow fatty acid choline | 30 | 110 |
| | 5-23 | Stearic acid monoglyceride | 10 | 118 |
| | 5-24 | Biotin | 5 | 106 |
| Comparative product | 5-1 | POE(20) sorbitan oleate | 50 | 72 |
| | 5-2 | Sodium succinate | 20 | 91 |
| | 5-3 | EDTA-4Na | 5 | 90 |
| Control area | | Only the culturing solution | — | 100 |

What is claimed is:

1. A method for assisting the growth of a plant, comprising the step of:

applying to the plant an effective amount of the plant-activating agent composition thereto, said plant-activating agent composition comprising:

(a) a plant-activating agent selected from the group consisting of:

(1) lipids or derivatives thereof, wherein said lipids or derivatives thereof are selected from the group consisting of monoacyl glycerol, diacyl glycerol, phosphatidylserines, phosphatidylethanolamines, sphingomyelin, phosphatidic acid, sphingolipid, glycolipid, terpenoid and sterols, (2) alcohols or derivatives thereof, wherein said alcohols or derivatives thereof are selected from the group consisting of distearyl ether, stearyl cetyl ether, ethylene glycol, diethylene glycol, polyethylene glycol, erythritol, pentaerythritol, pentitol, batyl alcohol, isostearyl glyceryl ether, behenyl glyceryl ether, N-lauroyl N-methylglucamide, and N-stearoyl N-methylglucamide, (3) amines or derivatives thereof, wherein said amines are selected from the group consisting of a primary, secondary and tertiary long chain amine, diamine and triamine having a $C_{8-30}$ alkyl group, or a salt thereof, and wherein said derivatives are selected from a quaternary ammonium salt, choline or a salt thereof, and a fatty acid salt of choline, (4) amino acids or derivatives thereof, wherein said amino acids or derivatives thereof are selected from the group consisting of ornithine derivatives, creatine derivatives, and acylated glutamine derivatives, (5) proteins or derivatives thereof, wherein said proteins or derivatives thereof are selected from the group consisting of glutathione, oxytocin, casein, keratin, hemoglobin, albumin and collagen, (6) nucleic acids or derivatives thereof, wherein said nucleic acids or derivatives thereof are selected from the group consisting of ribonucleic acids, deoxyribonucleic acids, decomposed products thereof, nucleoside phosphates thereof and nucleotides which are constituent units thereof, (7) natural extracts, wherein said natural extracts are selected from the group consisting of hinokitiol, chitin, chitosan, chlorella-decomposed products and wood vinegar, (8) fermentation residues, wherein said fermentation residues are selected from the group consisting of fermentation products obtained by mixed organic acid fermentation, glycerol fermentation and penicillin fermentation, and (9) vitamins wherein said vitamins are selected from the group consisting of coenzymes thereof, and vitamins A, D, E and K, wherein said agent shows not less than a 5% increase in unicellular green cell count within 15 days after an effective concentration of the plant activator has been given to a plant, wherein said increase in unicellular green cell count is calculated by the following formula:

Increase in unicellular green cell count (%)=[$(P_1-P_0)/P_0$]×100 wherein $P_0$ represents the count of unicellular green cells when the plant-activating agent is not used, and $P_1$ represents the count of unicellular green cells when the plant-activating agent is used; and (b) a surfactant, wherein said surfactant is at least one selected from an ester group-containing nonionic surfactant, an amphoteric surfactant, a carboxylic anionic surfactant, a phosphoric acid group-containing anonic surfactant and an ether group-containing non-ionic surfactant having no nitrogen atom, wherein said ether group-containing nonionic surfactant is at least one selected from a polyoxyalkylene alkyl ether, an alkyl(poly)glycoside and a polyoxyalkylene alkyl (poly)glycoside.

2. The method for assisting the growth of a plant as claimed in the claim 1, satisfying at least one of the following (a), (b), (c), (d) and (e):

(a) an improved degree of SPAD chlorophyll value of said plant of not less than two points, (b) an increase in the weight of said plant of not less than 10%, wherein the weight of said plant is either a fresh weight or a dry weight, (c) an improved degree of leaf-area of said plant of not less than 5%, (d) an increase in the concentration amount of ascorbic acid in a blade part of said plant of not less than 5%, and (e) a decrease in the concentration amount of nitrate ion in a blade part of said plant of not less than 10%.

3. The method for assisting the growth of a plant of claim 1 or claim 2, wherein said unicellular green cells are chlorella and said substance has not less than a 5% increase in unicellular green cell count of said chlorella.

4. The method for assisting the growth of a plant of claim 1 or claim 2, wherein said agent is given in the form of an aqueous solution or an aqueous dispersion in an amount of 1 to 500 ppm.

5. The method for assisting the growth of a plant of claim 1 or claim 2, wherein said agent is given by spraying in the form of a solid agent that in a granular form, a dust formulation, an aqueous solution or an aqueous dispersion of the plant-activating agent, and is given as an active component in a proportion of 0.001 to 3000 kg per 1000 m².

6. The method for assisting the growth of a plant of claim 1 or claim 2, and said plant-activating agent composition further comprising a chelating agent.

7. The method for assisting the growth of a plant of claim 1 or claim 2, wherein a ratio by weight of said surfactant to said plant-activating agent is from 0.01 to 100.

8. The method for assisting the growth of a plant of claim 1 or claim 2, wherein a HLB of said surf actant is not less than 10.

9. The method for assisting the growth of a plant of claim 1 or claim 2, wherein said method comprises the step of giving said effective amount of the plant-activating agent directly as a solid fertilizer in the form of a dust formulation or a granule formulation.

10. The method for assisting the growth of a plant of claim 1 or claim 2, wherein said method comprises the step of spraying a diluted aqueous solution containing said effective amount of the plant-activating agent directly on phylloplanes, stems or fruits of said plant.

11. The method for assisting the growth of a plant of claim 1 or claim 2, wherein said method comprises the step of injecting a diluted aqueous solution containing said effective amount of the plant-activating agent into soil.

12. The method for assisting the growth of a plant of claim 1 or claim 2, wherein said method comprises the step of contacting the roots to said plant with water that includes therein a diluted and mixed aqueous liquid for hydroponics that contains said effective amount of the plant-activating agent.

13. A method for assisting the growth of a plant, comprising the step of:

applying to the plant an effective amount of the plant-activating agent composition thereto, said plant-activating agent composition comprising:

(a) a plant-activating agent selected from the group consisting of:

(1) lipids or derivatives thereof, wherein said lipids or derivatives thereof are selected from the group consisting of monoacyl glycerol, diacyl glycerol, phosphatidylserines, phosphatidylethanolamines, sphingomyelin, phosphatidic acid, sphingolipid, glycolipid, terpenoid and sterols, (2) alcohols or derivatives thereof, wherein said alcohols or derivatives thereof are selected from the group consisting of distearyl ether, stearyl cetyl ether, ethylene glycol, diethylene glycol, polyethylene glycol, erythritol, pentaerythritol, pentitol, batyl alcohol, isostearyl glyceryl ether, behenyl glyceryl ether, N-lauroyl N-methylglucamide, and N-stearoyl N-methylglucamide, (3) amines or derivatives thereof, wherein said amines are selected from the group consisting of a primary, secondary and tertiary long chain amine, diamine and triamine having a $C_{8-30}$ alkyl group, or a salt thereof, and wherein said derivatives are selected from a quaternary ammonium salt, choline or a salt thereof, and a fatty acid salt of choline, (4) amino acids or derivatives thereof, wherein said amino acids or derivatives thereof are selected from the group consisting of ornithine derivatives, creatine derivatives, and acylated glutamine derivatives, (5) proteins or derivatives thereof, wherein said proteins or derivatives thereof are selected from the group consisting of glutathione, oxytocin, casein, keratin, hemoglobin, albumin and collagen, (6) nucleic acids or derivatives thereof, wherein said nucleic acids or derivatives thereof are selected from the group consisting of ribonucleic acids, deoxyribonucleic acids, decomposed products thereof, nucleoside phosphates thereof and nucleotides which are constituent units thereof, (7) natural extracts, wherein said natural extracts are selected from the group consisting of hinokitiol, chitin, chitosan, chlorella-decomposed products and wood vinegar, (8) fermentation residues, wherein said fermentation residues are selected from the group consisting of fermentation products obtained by mixed organic acid fermentation, glycerol fermentation and penicillin fermentation, and (9) vitamins wherein said vitamins are selected from the group consisting of coenzymes thereof, and vitamins A, D, E and K, wherein said agent shows not lees than a 5% increase in green cell count of a callus of green cells within 15 days after an effective concentration of the plant activator has been given to a plant, wherein said increase in green cell count is calculated by the following formula:

$$\text{Increase in green cell count of a callus of green cells (\%)} = [(P_1 - P_0)/P_0] \times 100$$

wherein $P_0$ represents the count of green cells of a callus of green cells when the plant-activating agent is not used, and $P_1$ represents the count of green cells of a callus of green cells when the plant-activating agent is used; and (b) a surfactant, wherein said surfactant is at least one selected from an ester group-containing nonionic surfactant, an amphoteric surfactant, a carboxylic anionic surfactant, a phosphoric acid group-containing anonic surfactant and an ether group-containing nonionic surfactant having no nitrogen atom, wherein said ether group-containing nonionic surf actant is at least one selected from a polyoxyalkylene alkyl ether, an alkyl(poly)glycoside and a polyoxyalkylene alkyl (poly)glycoside.

14. The method for assisting the growth of a plant as claimed in the claim 13, satisfying at least one of the following (a), (b), (c), (d) and (e):

(a) an improved degree of SPAD chlorophyll value of said plant of not less than two points, (b) an increase in the weight of said plant of not less than 10%, wherein the weight of said plant is either a fresh weight or a dry weight, (c) an improved degree of leaf-area of said plant of not less than 5%, (d) an increase in the concentration amount of ascorbic acid in a blade part of said plant of not less than 5%, and (e) a decrease in the concentration amount of nitrate ion in a blade part of said plant of not less than 10%.

15. The method for assisting the growth of a plant of claim 13 or claim 14, wherein said callus of green cells is a liverwort and said substance has not less than a 5% increase in green cell count of said liverwort callus.

16. The method for assisting the growth of a plant of claim 13 or claim 14, wherein said agent is given in the form of an aqueous solution or an aqueous dispersion in an amount of 1 to 500 ppm.

17. The method for assisting the growth of a plant of claim 13 or claim 14, wherein said agent is given by spraying in the form of a solid agent that in a granular form, a dust formulation, an aqueous solution or an aqueous dispersion of the plant-activating agent, and is given as an active component in a proportion of 0.001 to 3000 kg per 1000 m$^2$.

18. The method for assisting the growth of a plant of claim 13 or claim 14, and said plant-activating agent composition further comprising a chelating agent.

19. The method for assisting the growth of a plant of claim 13 or claim 14, wherein a ratio by weight of said surfactant to said plant-activating agent is from 0.01 to 100.

20. The method for assisting the growth of a plant of claim 13 or claim 14, wherein a HLB of said surfactant is not less than 10.

21. The method for assisting the growth of a plant of claim 13 or claim 14, wherein said method comprises the step of giving said effective amount of the plant-activating agent directly as a solid fertilizer in the form of a dust formulation or a granule formulation.

22. The method for assisting the growth of a plant of claim 13 or claim 14, wherein said method comprises the step of spraying a diluted aqueous solution containing said effective amount of the plant-activating agent directly on phylloplanes, stems or fruits of said plant.

23. The method for assisting the growth of a plant of claim 13 or claim 14, wherein said method comprises the step of injecting a diluted aqueous solution containing said effective amount of the plant-activating agent into soil.

24. The method for assisting the growth of a plant of claim 13 or claim 14, wherein said method comprises the step of contacting the roots to said plant with water that includes therein a diluted and mixed aqueous liquid for hydroponics that contains said effective amount of the plant-activating agent.

* * * * *